United States Patent
Jones

(10) Patent No.: US 9,689,815 B2
(45) Date of Patent: Jun. 27, 2017

(54) XRF ANALYZER ROTATIONAL FILTER

(71) Applicant: Moxtek, Inc., Orem, UT (US)

(72) Inventor: Vincent Floyd Jones, Cedar Hills, UT (US)

(73) Assignee: Moxtek, Inc., Orem, UT (US)

( * ) Notice: Subject to any disclaimer, the term of this patent is extended or adjusted under 35 U.S.C. 154(b) by 217 days.

(21) Appl. No.: 14/806,975

(22) Filed: Jul. 23, 2015

(65) Prior Publication Data

US 2016/0078974 A1    Mar. 17, 2016

Related U.S. Application Data

(60) Provisional application No. 62/049,781, filed on Sep. 12, 2014.

(51) Int. Cl.
*G01N 23/223* (2006.01)
*G21K 1/02* (2006.01)
*G21K 1/10* (2006.01)

(52) U.S. Cl.
CPC ............. *G01N 23/223* (2013.01); *G21K 1/02* (2013.01); *G21K 1/10* (2013.01)

(58) Field of Classification Search
CPC .. G01N 2223/301; G01N 23/223; G21K 1/02; G21K 1/04; G21K 1/10
See application file for complete search history.

(56) References Cited

U.S. PATENT DOCUMENTS

| | | | | |
|---|---|---|---|---|
| 6,909,770 | B2* | 6/2005 | Schramm | G01N 23/223 378/44 |
| 7,430,274 | B2* | 9/2008 | Connors | G01N 23/223 378/102 |
| 7,899,153 | B2 | 3/2011 | Dugas et al. | |
| 8,155,268 | B2* | 4/2012 | Pesce | G01N 23/223 378/45 |
| 8,494,113 | B2 | 7/2013 | Grodzins | |
| 2004/0136500 | A1 | 7/2004 | Amemiya et al. | |
| 2010/0150307 | A1 | 6/2010 | Grodzins | |
| 2011/0007869 | A1 | 1/2011 | Gendreau et al. | |
| 2011/0096898 | A1 | 4/2011 | Kharchenko et al. | |

FOREIGN PATENT DOCUMENTS

JP    2013/221745 A    10/2013

* cited by examiner

*Primary Examiner* — David J Makiya
*Assistant Examiner* — Soorena Kefayati
(74) *Attorney, Agent, or Firm* — Thorpe, North & Western, LLP

(57) ABSTRACT

An XRF analyzer can include a rotatable filter structure to separately position at least two different x-ray source modification regions between an x-ray source and a focal point and at least two different x-ray detector modification regions between an x-ray detector and the focal point.

An XRF analyzer can include a rotatable source filter wheel between an x-ray source and a focal point and a rotatable detector filter wheel between an x-ray detector and the focal point. The source filter wheel can include multiple x-ray source modification regions. The detector filter wheel can include multiple x-ray detector modification regions. A gear wheel can mesh with a gear on the source filter wheel and with a gear on the detector filter wheel and can cause the source filter wheel and the detector filter wheel to rotate together.

20 Claims, 7 Drawing Sheets

XRF ANALYZER ROTATIONAL FILTER

CLAIM OF PRIORITY

This claims priority to U.S. Provisional Patent Application No. 62/049,781, filed on Sep. 12, 2014, which is hereby incorporated herein by reference in its entirety.

FIELD OF THE INVENTION

The present application is related generally to x-ray fluorescence (XRF) analyzers.

BACKGROUND

In x-ray fluorescence (XRF) analysis, x-rays are emitted from an x-ray source to a sample. The sample can receive x-rays from the source then fluoresce x-rays that have an energy spectrum specific to chemical elements in the sample. An x-ray detector can receive these x-rays emitted from the sample. The detector, along with associated electronics, can analyze these x-rays to determine chemical composition of the sample.

It can be difficult in the analysis to determine elements in low concentrations. It can also be difficult to distinguish between elements that emit similar energy spectra. Filtration of x-rays emitted from the source can improve analysis in these situations. Filtration of x-rays can provide a narrow energy band specific to a target element, allowing easier detection of that element. A user of an XRF analyzer typically would use the analyzer for detection of multiple, different elements. Thus, the user might desire different filters for different applications.

It is sometimes desirable to do an XRF analysis of a small sample. X-rays from the source that impinge on material surrounding the sample can result in undesirable noise because these surrounding materials can also fluoresce x-rays to the detector. It would be beneficial in these situations to narrow the x-ray beam to a smaller size.

An XRF analysis typically includes energizing the x-ray source to allow the x-ray source to emit x-rays. Energizing the x-ray source can include application of a high voltage across an x-ray tube and heating a filament. Energizing the x-ray source for each use takes time. It can be beneficial to a user to minimize the time required for each analysis.

After each analysis, the x-ray source is typically de-energized. Until this energy drops below a certain threshold, x-rays can continue to emit from the x-ray source. This can be a safety concern for a user who might not be aware of such continued emission. It would be beneficial to improve XRF analysis safety.

Portable XRF analyzers are often used in harsh environments where delicate windows on the x-ray source or the x-ray detector can be damaged by sharp objects or corrosive materials. It would be beneficial to protect the x-ray source and the x-ray detector from damage.

Vibration of the x-ray source or the x-ray detector in an XRF analyzer can adversely affect analysis results. It can be beneficial to avoid or minimize vibration of the x-ray source and the x-ray detector caused by moving components.

SUMMARY

It has been recognized that it would be advantageous to provide multiple, different filters for x-rays emitted from the x-ray source; to provide a means of narrowing the x-ray beam; to minimize the time required for each analysis; to improve XRF analysis safety; to avoid or minimize vibration of the x-ray source and the x-ray detector; and to protect the x-ray source and the x-ray detector from damage. The present invention is directed to various embodiments of x-ray fluorescence (XRF) analyzers that satisfy these needs. Each embodiment can satisfy one, some, or all of these needs.

The XRF analyzer can comprise an x-ray source having an x-ray emission end, and an x-ray detector having an x-ray receiving end, both carried by a housing. The x-ray source can be positioned and oriented to emit x-rays from the x-ray emission end towards a focal point. The x-ray detector can be positioned and oriented to face the focal point, and can be configured to receive, through the x-ray receiving end, fluoresced x-rays emitted from a sample disposed at the focal point.

In one embodiment, the XRF analyzer can further comprise a rotatable filter structure disposed between the x-ray emission end and the focal point and disposed between the x-ray receiving end and the focal point. The filter structure can be rotatable to separately position x-ray source modification region(s) between the x-ray emission end and the focal point and x-ray detector modification region(s) between the x-ray receiving end and the focal point.

In another embodiment, the XRF analyzer can further comprise a rotatable source filter wheel disposed between the x-ray emission end and the focal point and a rotatable detector filter wheel disposed between the x-ray receiving end and the focal point. The source filter wheel can include multiple x-ray source modification regions. The detector filter wheel can include multiple x-ray detector modification regions. The source filter wheel and the detector filter wheel can each have a gear at an outer perimeter. The XRF analyzer can further comprise a gear wheel which can mesh with the gear on the source filter wheel and the gear on the detector filter wheel. The gear wheel can be configured to cause the source filter wheel and the detector filter wheel to rotate together.

DETAILED DESCRIPTION

Figure 1:
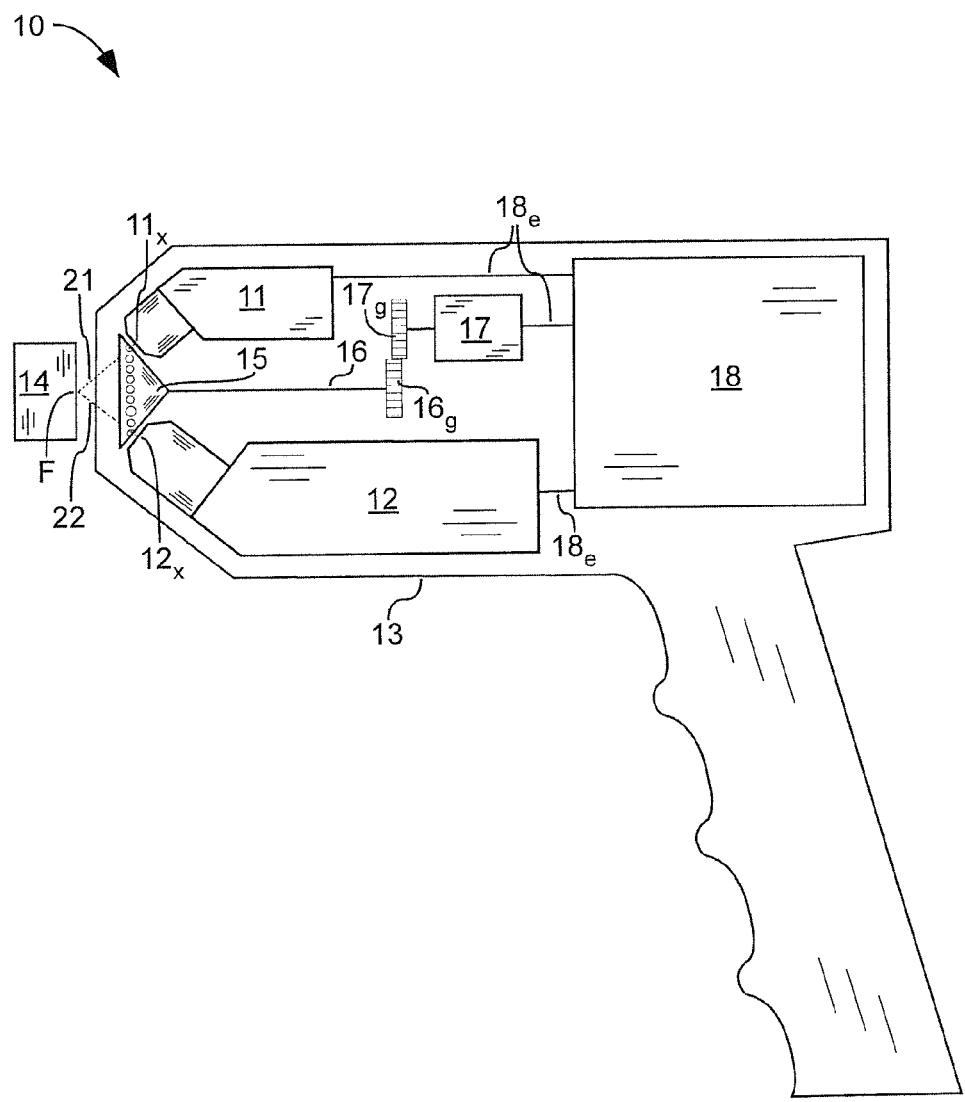
FIG. 1 is a schematic cross-sectional side view of a XRF analyzer with a rotatable filter structure, in accordance with an embodiment of the present invention.

As illustrated in FIGS. 1, 2, 3, and 7, x-ray fluorescence (XRF) analyzers 10 and 70 can comprise an x-ray source 12 having an x-ray emission end $12_x$, and an x-ray detector 11 having an x-ray receiving end $11_x$, both carried by a housing 13. The x-ray source 12 can be positioned and oriented to emit x-rays 22 from the x-ray emission end $12_x$ towards a focal point F. The x-ray detector 11 can be positioned and oriented to face the focal point F, and can be configured to receive, through the x-ray receiving end $11_x$, fluoresced x-rays 21 emitted from a sample 14 disposed at the focal point F.

Figure 2:
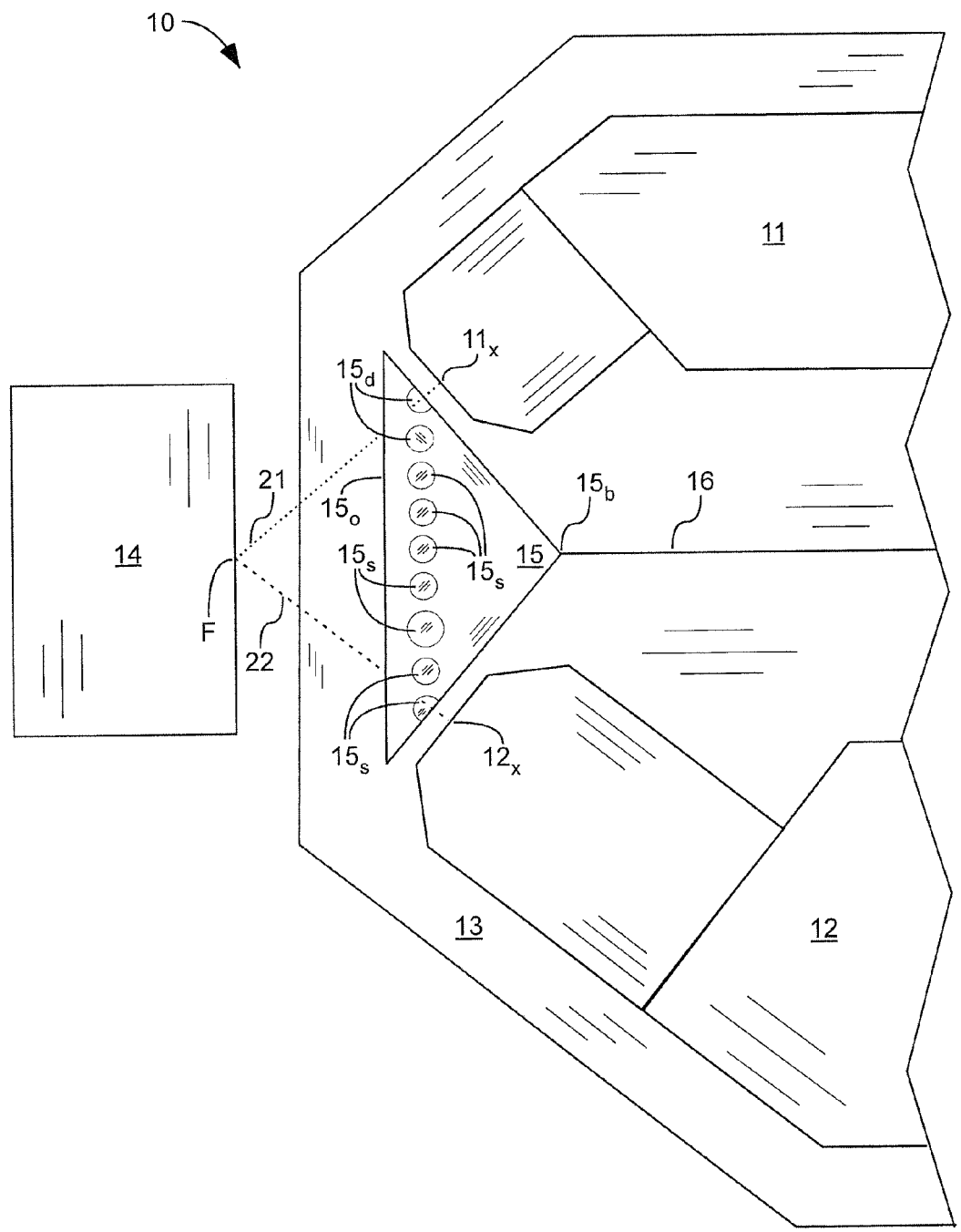
FIGS. 2-3 are schematic cross-sectional side views of portions of the XRF analyzer of FIG. 1, in accordance with embodiments of the present invention.
Figure 3:
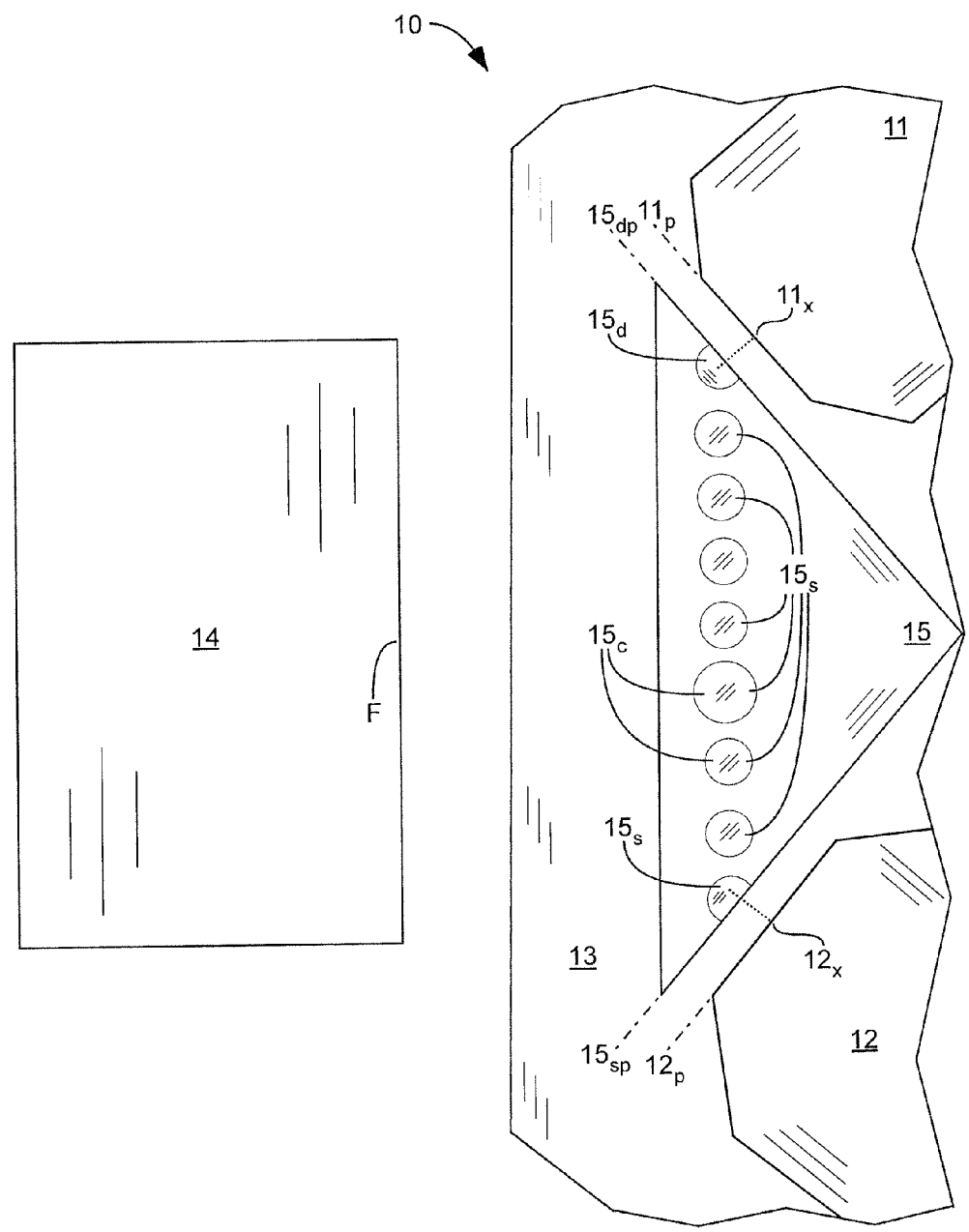

As shown in FIGS. 1-3, a rotatable filter structure 15 can be disposed between the x-ray emission end $12_x$ and the focal point F and disposed between the x-ray receiving end $11_x$ and the focal point F. The filter structure 15 can be rotatable to separately position at least two different x-ray source modification regions $15_s$ between the x-ray emission end $12_x$ and the focal point F and at least two different x-ray detector modification regions $15_d$ between the x-ray receiving end $11_x$ and the focal point F. The filter structure 15 can have a material and thickness configured to substantially block x-rays from being emitted through the filter structure 15 except through certain source modification regions $15_s$ and detector modification regions $15_d$ designed for x-ray 21 transmission therethrough. The source modification regions $15_s$ and the x-ray detector modification regions $15_d$ can provide many benefits, as will be described in the following several paragraphs.

The source modification regions $15_s$ can include multiple, different, solid x-ray filters. For example, one filter can be made of a different material than other filter(s). X-rays 22 emitted from the x-ray source 12 can pass through the filter, thus filtering the x-rays 22 and providing a relatively narrow energy band specific to a target element, allowing easier detection of that element. X-ray source modification regions $15_s$ can include a first, solid x-ray filter configured to filter x-rays for one x-ray energy band and a second, solid x-ray filter configured to filter x-rays for a different x-ray energy band.

Another example of different filters is that one filter can have a different thickness than other filter(s). There can be multiple filters, all made of the same material, but having different thicknesses. Having a thicker overall filter can allow for more accurate analysis of a narrow energy band but increases time of analysis. In some situations, the more accurate analysis outweighs the problem of increased time. Filters can be made of any solid material that can be formed into a thin film or window. Filters are typically a metal or metal alloy, such as for example silver, gold, rhodium, iron, copper, aluminum, tin, etc.

It is sometimes desirable to do an XRF analysis of a small sample. X-rays from the source that impinge on material surrounding the sample can result in undesirable noise because these surrounding materials can also fluoresce x-rays to the detector. The source modification regions $15_s$ can include multiple, different, sized collimators $15_c$. For example, the collimators $15_c$ can include a first collimator having a first diameter and a second collimator having a second diameter. The first diameter can be substantially different from the second diameter in order to provide a different x-ray collimation at the first collimator relative to the second collimator. Multiple, different sized collimators $15_c$ can allow collimation of the x-ray beam 22 to different diameters for different applications. The different collimators $15_c$ can be tubes of different lengths. The collimators $15_c$ can be open holes (i.e. no solid material) or can be x-ray windows. A collimator $15_c$ and filter can be combined to both collimate and filter the x-rays 22.

The source modification regions $15_s$ can include a solid blocking structure having a material (e.g. high atomic number) and thickness configured to substantially block x-rays from being emitted through the blocking structure. Between separate analyses, the XRF analyzer can be programmed to rotate the filter structure to place the blocking structure in front of the x-ray emission end $12_x$. This can allow the x-ray source 12 to continue to emit x-rays 22 between analyses instead of fully de-energizing the x-ray source. The x-ray source 12 would then be ready (or ready very quickly if there was only partial de-energizing) for the next analysis. By avoiding the need to fully energize and fully de-energize the x-ray source 12 between each analysis, required time for completion of each analysis can be reduced.

The blocking structure can also improve user safety. If the x-ray source 12 is de-energized following an individual analysis, x-rays can continue to emit from the x-ray source until energy of the x-ray source 12 drops below a certain threshold. This can be a safety concern for a user who might not be aware of such continued emission. By blocking x-rays 22 with a blocking structure at the end of each analysis, XRF analyzer user safety can be improved.

Portable XRF analyzers are often used in harsh environments where delicate windows on the x-ray source can be damaged by sharp objects or corrosive materials. The source modification regions $15_s$ can include a protective structure. The protective structure can comprise a solid, protective material configured to protect the x-ray source 12 from damage by solid objects. For example, the protective structure can be a sheet of metal. The blocking structure and the protective structure can be the same source modification regions $15_s$, to both block x-rays and to protect the x-ray source 12 from damage. Alternatively, the protective structure can be a solid x-ray window having a material and thickness to allow x-rays to substantially pass therethrough, but made of a material to substantially protect the x-ray source, such as protection against corrosive chemicals for example.

The detector modification regions $15_d$ can include a solid, protective structure configured to protect the x-ray detector 11 from damage by solid objects. The detector modification regions $15_d$ can also include an aperture configured to allow x-rays to pass therethrough. The aperture can be various shapes, including a round hole or an elongated slot. The aperture can be an opening with no solid material. Alternatively, the aperture can be a solid x-ray window having a material and thickness to allow x-rays to substantially pass therethrough. The solid window aperture can be made of a material to substantially protect the x-ray detector 11 against corrosive chemicals. This solid window aperture can be useful if the XRF analyzer is used in harsh, chemical environments. Thus, during an XRF analysis, the filter structure 15 can be rotated to place an aperture between the x-ray receiving end $11_x$ and the focal point F, then after an analysis or between different analyses, the filter structure 15 can be rotated to place a protective structure between the x-ray receiving end $11_x$ and the focal point F. At least one of the modification regions can be used as either a detector modification region $15_d$ or a source modification region $15_s$.

A shaft 16 can be attached to the filter structure 15. The shaft 16 can be attached to a base end $15_b$ of the filter structure 15. A motor 17 with a gear $17_g$ can mesh with a gear $16_g$ on the shaft 16 to cause the shaft 16 to rotate, and thus also causing the filter structure 15 to rotate to separately position the source modification regions $15_s$ between the x-ray emission end $12_x$ and the focal point F and the detector modification regions $15_d$ between the x-ray receiving end $11_x$ and the focal point F.

As just described, the filter structure 15 can provide many benefits to XRF analysis. An additional benefit by use of this filter structure 15 can be avoidance of vibration which can adversely affect XRF analysis. Vibration of the x-ray source 12 or the x-ray detector 11 can adversely affect analysis results. A single filter structure 15 for both the x-ray source 12 and the x-ray detector 11 can be placed in a central location of the XRF analyzer 10 and need not be directly attached to either the x-ray source 12 or the x-ray detector 11. It is possible to not attach the filter structure 15 directly on the x-ray source 12 or the x-ray detector 11. This can minimize or avoid adversely affecting XRF analysis by vibration as the filter structure turns. The filter structure 15 and/or the motor 17 can be mounted on the housing 13 with vibration isolation devices or pads, thus further minimizing the effect this vibration can have on XRF analysis.

As shown in FIG. 3, the filter structure 15 can be shaped and located to position the source modification regions $15_s$ such that a plane $15_{sp}$ of the source modification regions $15_s$ is substantially parallel to a face $12_p$ of the x-ray emission end $12_x$. The filter structure 15 can also be shaped and located to position the detector modification regions $15_d$ such that a plane $15_{dp}$ of the detector modification regions $15_d$ is substantially parallel to a face $11_p$ of the x-ray receiving end $11_x$. These parallel-relationships can be maintained as the filter structure 15 rotates. For example, a three-dimensional cone-shaped filter structure 15 could be shaped and positioned for this alignment. This parallel alignment as described above can allow adequate filtration, collimation, protection, or blocking of x-rays.

The filter structure 15 can have various shapes. The filter structure 15 can be solid except for channels for x-rays to pass in some of the modification regions. Alternatively, the filter structure 15 can have a shape like a cup with a concave portion or hollow and thus can also be called a filter cup. A choice of whether to use a solid filter structure or a hollow filter cup can depend on factors such as weight requirements; effectiveness at blocking, filtering, collimating, and protecting; and manufacturability.

Figure 4:
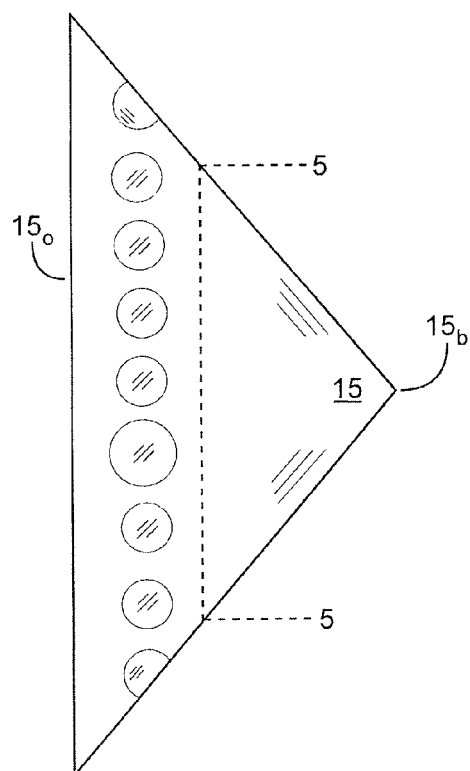
FIG. 4 is a schematic side view of a filter structure, in accordance with an embodiment of the present invention.
Figure 5A:
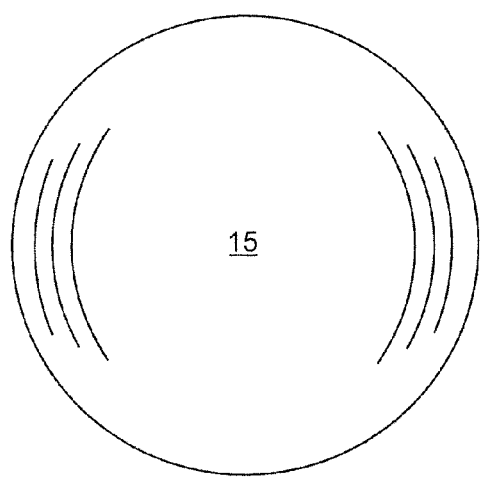
FIGS. 5*a-b* are schematic end views of the filter structure of FIG. 4 taken along line 5-5 in FIG. 4, in accordance with embodiments of the present invention.
Figure 5B:
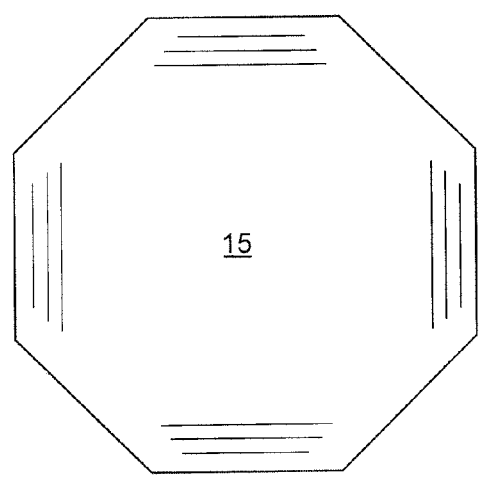

As shown in FIG. 4, the filter structure 15 can taper down in diameter from an open end $15_o$ to a base end $15_b$. The filter structure 15 can be cone-shaped or frustum-shaped. As shown in FIG. 5a, a cross section of the filter structure 15 at any point from the open end $15_o$ to the base end $15_b$ can have a circular shape. As shown in FIG. 5b, a cross section of the filter structure 15 at any point between the open end $15_o$ and the base end $15_{vb}$ can have a polygon shape. All sides of the polygon shape can be substantially equal in size. If the cross section is a polygon shape, then source modification regions $15_s$ and x-ray detector modification regions $15_d$ can be disposed at faces of the polygon shape. A choice of filter structure 15 shape can be made based on the shape's effect on blocking, filtering, collimating, and protecting; manufacturability; or the cost of the filter structure 15.

Figure 6:
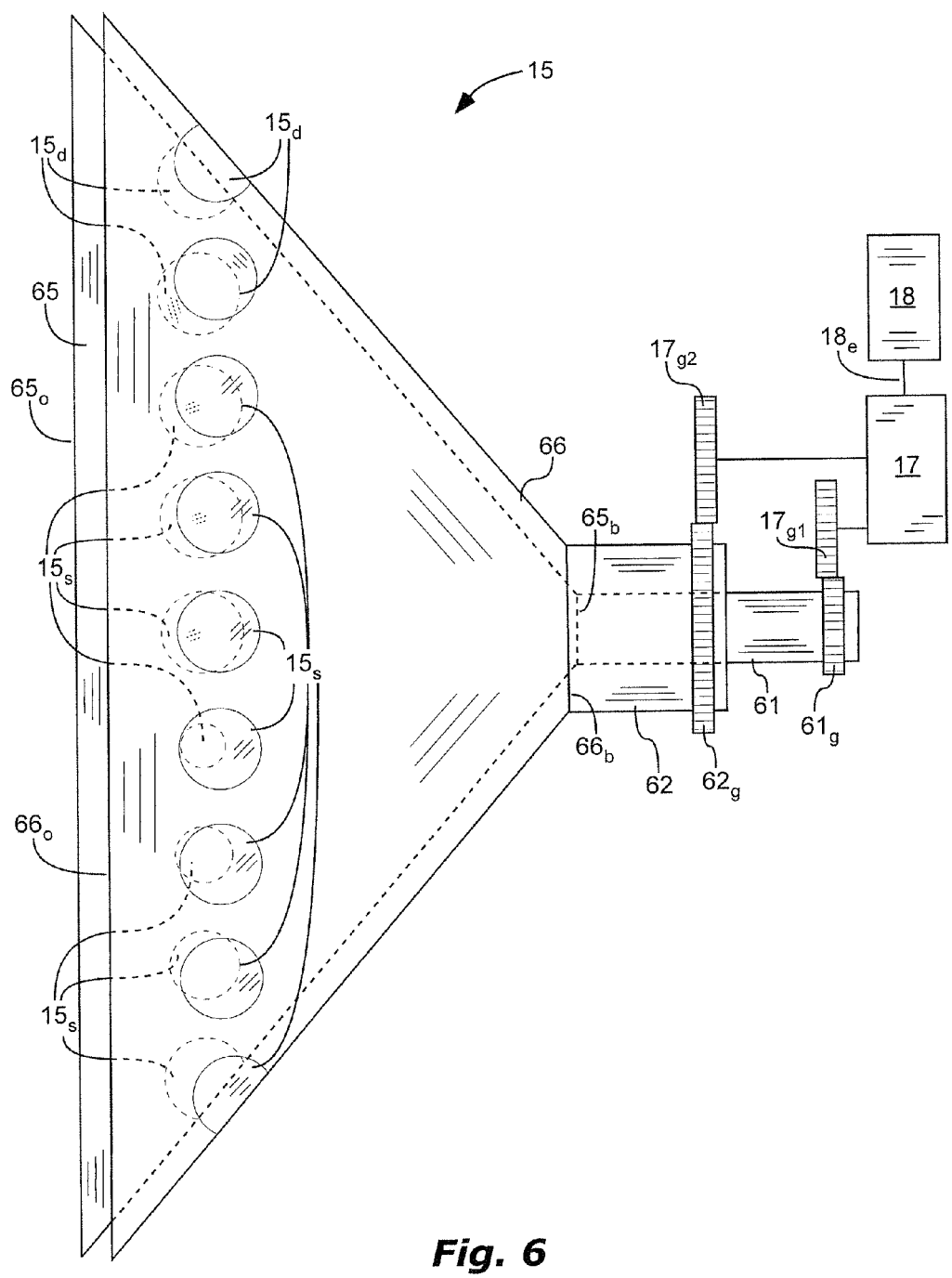
FIG. 6 is a schematic side view of a filter structure including an inner cup disposed at least partially inside of an outer cup, in accordance with an embodiment of the present invention.

As shown in FIG. 6, the filter structure 15 can include an inner cup 65 disposed at least partially inside of an outer cup 66. The inner cup 65 and the outer cup 66 can each have at least two of the source modification regions $15_s$ and at least one of the detector modification regions $15_d$. The inner cup and/or the outer cup can have at least two of the detector modification regions $15_d$. Use of both the inner cup 65 and the outer cup 66 can allow multiple filters that each can combine with any one of multiple collimators. For example, the source modification regions $15_s$ on one of the inner cup 65 or the outer cup 66 can include multiple, different filters, and the source modification regions $15_s$ on the other of the inner cup 65 or the outer cup 66 can include multiple, different collimators. As another example, the source modification regions $15_s$ on one of the inner cup 65 or the outer cup 66 can have filters of the same material, which can be aligned for a thicker overall filter.

Both the inner cup 65 and the outer cup 66 can include a detector modification region $15_d$ that is an aperture to allow x-rays to pass. At least one of the inner cup 65 or the outer cup 66 can include a detector modification region $15_d$ that is a solid, protective structure to protect the detector 11 from damage.

The inner cup 65 and the outer cup 66 can be rotatable to separately position the source modification regions $15_s$ between the x-ray emission end $12_x$ and the focal point F and the detector modification region(s) $15_d$ between the x-ray receiving end $11_x$ and the focal point F. The inner cup 65 and the outer cup 66 can each have a base end $65_b$ and $66_b$ opposite of an open end $65_o$ and $66_o$. The open ends $65_o$ and $66_o$ of both the inner cup 65 and the outer cup 66 can be disposed between the x-ray emission end $12_x$ and the focal point F and between the x-ray receiving end $11_x$ and the focal point F. A convex portion of the inner cup 65 can nest within a concave portion of the outer cup 66.

The inner cup 65 and the outer cup 66 can be supported and rotated by dual, concentric, tubes 61 and 62. An inner tube 61 can connect to the inner cup 65. The inner tube 61 can be configured to rotate with the inner cup 65 and can cause the inner cup 65 to rotate. An outer tube 62 can connect to the outer cup 66. The outer tube 62 can be configured to rotate with the outer cup 66 and can cause the outer cup 66 to rotate. A motor 17 can have two gears $17_{g1}$ and $17_{g2}$ that can mesh with gears $61_g$ and $62_g$ on the inner tube 61 and the outer tube 62, respectively. The motor 17 can be configured to cause the inner tube 65 and the outer tube 66 to rotate independently, thus allowing certain source modification regions $15_s$ (e.g. filter) on the inner cup 65 to align with certain source modification regions $15_s$ (e.g. collimator) on the outer cup 66.

Figure 7:
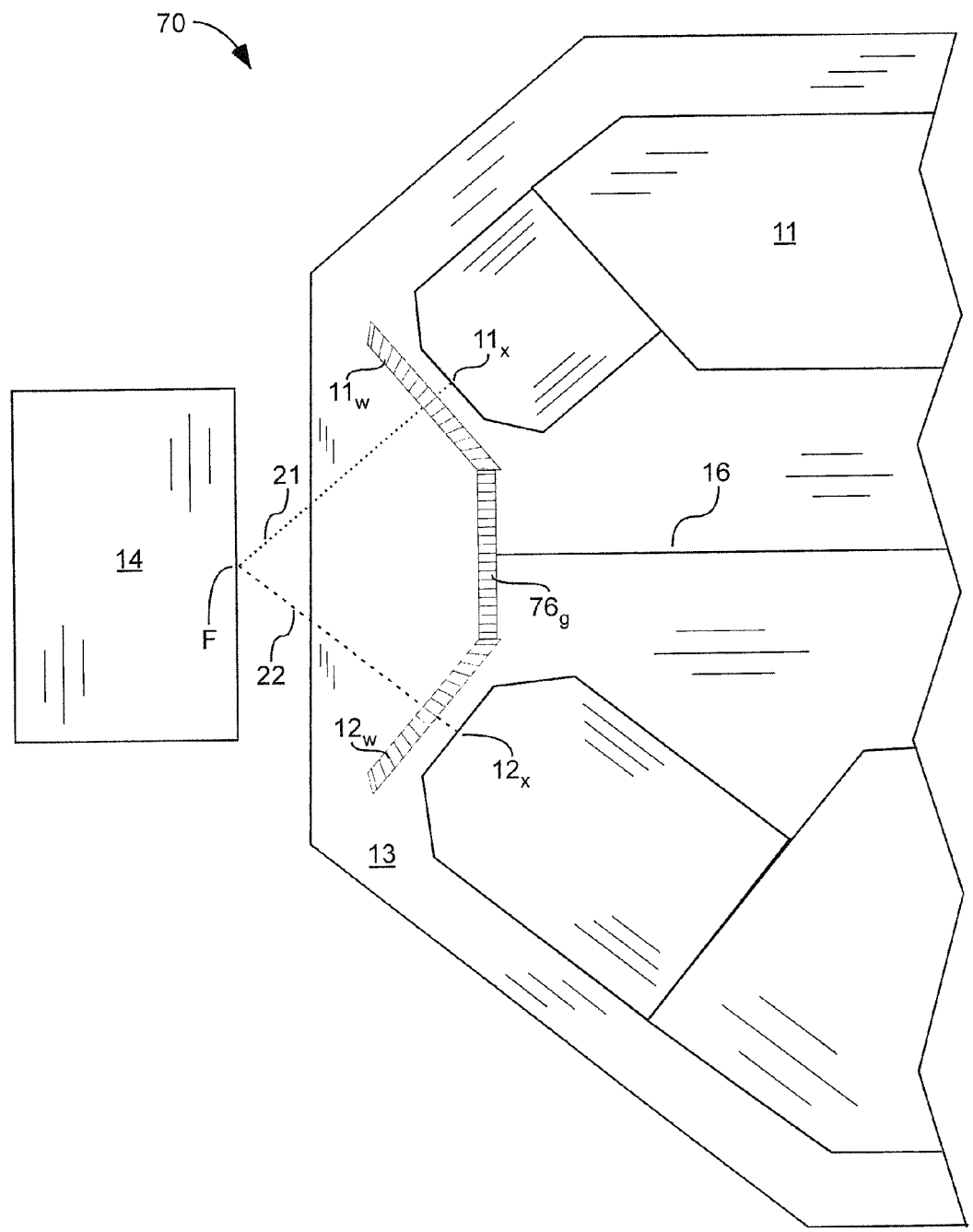
FIG. 7 is a schematic cross-sectional side view of a XRF analyzer showing a gear wheel meshing with a detector filter wheel and a source filter wheel, in accordance with an embodiment of the present invention.
Figure 8:
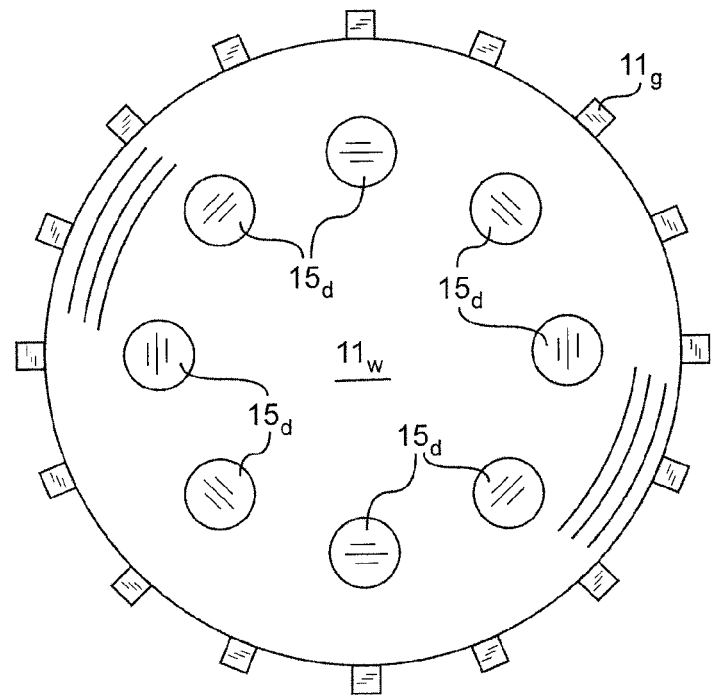
FIG. 8 is a schematic top view of a detector filter wheel, in accordance with an embodiment of the present invention.
Figure 9:
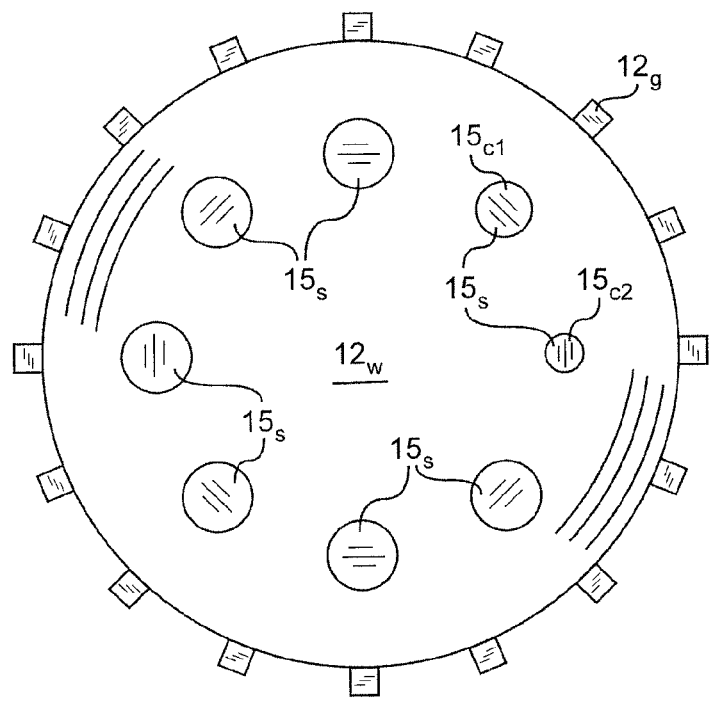
FIG. 9 is a schematic top view of a source filter wheel in accordance with an embodiment of the present invention.

As shown in FIGS. 7-9, a rotatable source filter wheel $12_w$ can be carried by the housing 13 and can be disposed between the x-ray emission end $12_x$ and the focal point F. The source filter wheel $12_w$ can include multiple, different x-ray source modification regions $15_s$ including at least one of:

1. a first, solid x-ray filter configured to filter x-rays for one x-ray energy band and a second, solid x-ray filter configured to filter x-rays for a different x-ray energy band;
2. a first, solid x-ray filter having a different thickness than a second, solid x-ray filter;
3. a first collimator $15_{c1}$ having a first diameter and a second collimator $15_{c2}$ having a second diameter wherein the first diameter is substantially different from the second diameter in order to provide a different x-ray collimation at the first collimator $15_{c1}$ relative to the second collimator $15_{c2}$;
4. a solid blocking structure having a material and thickness configured to substantially block x-rays 22 from being emitted through the blocking structure;
5. a protective structure comprising a solid, protective material configured to protect the x-ray source 12 from damage by solid objects; or
6. combinations thereof.

The filter(s), the collimator(s), the solid blocking structure, and the protective structure can have characteristics and benefits as described above in reference to the filter structure 15.

Also shown in FIG. 7-9, a rotatable detector filter wheel 11$_w$ can be carried by the housing 13 and can be disposed between the x-ray receiving end 11$_x$ and the focal point F. The detector filter wheel 11$_w$ can include multiple, different x-ray detector modification regions 15$_d$ including:
1. a protective structure comprising a solid, protective material configured to protect the x-ray detector 11 from damage by solid objects; and
2. an aperture configured to allow x-rays to pass therethrough.

The source filter wheel 12$_w$ and the detector filter wheel 11$_w$ can each have a gear 12$_g$ and 11$_g$ at an outer perimeter. A gear wheel 76$_g$ can mesh with the gear 12$_g$ on the source filter wheel 12$_w$ and with the gear 11$_g$ on the detector filter wheel 11$_w$. Thus, the gear wheel 76$_g$ can be configured to cause the source filter wheel 12$_w$ and the detector filter wheel 11$_w$ to rotate together. "Together", as used in this context, means both filter wheels 11$_w$ and 12$_w$ rotate at the same time, caused by the rotation of the gear wheel 76$_g$; however, "together" does not necessarily mean that both filter wheels 11$_w$ and 12$_w$ rotate in the same direction or for the same angular displacement. The term "mesh" as used in this context, means that the filter wheels 11$_w$ and 12$_w$ and the gear wheel 76$_g$ directly contact each other or that the gear wheel 76$_g$ directly contacts one or more intermediate gears and one of the intermediate gears directly contacts the filter wheels 11$_w$ and 12$_w$. In either case, this meshing of the gear wheel 76$_g$ with the filter wheels 11$_w$ and 12$_w$ can result in rotation of the filter wheels 11$_w$ and 12$_w$ as the gear wheel 76$_g$ rotates.

The gear wheel 76$_g$ can be attached to a shaft 16 which can be attached to a motor 17 (see FIG. 1). The motor 17 can cause the gear wheel 76$_g$, and thus also the filter wheels 11$_w$ and 12$_w$, to rotate. As described below, an electronic processor 18 can control the motor 17.

The various embodiments of XRF analyzers described above can further comprise an electronic processor 18 (see FIG. 1). The electronic processor 18 can be configured to receive a program input by a user and to select and position the source modification regions 15$_s$ and the detector modification regions 15$_d$ based on the program. The electronic processor 18 can be configured to analyze x-rays 21 received by the x-ray detector 11 (defining an analysis) and to select and position the source modification regions 15$_s$ based on the analysis.

A method of using the various embodiments of XRF analyzers described above can comprise the following steps, and can be performed in the following order:
1. inputting a guess of a material of a sample 14 to be analyzed into the XRF analyzer;
2. allowing the XRF analyzer to automatically select one of the source modification regions 15$_s$ based on the guess;
3. analyzing the sample 14 (defining an analysis); and
4. changing the selected source modification region 15$_s$ based on initial results of the analysis.

Some or all of the above description, and the following claims, may also be applicable to laser-induced breakdown spectroscopy (LIBS), x-ray diffraction (XRD) analyzers, and Raman spectroscopy tools. The term "XRF analyzer" used herein can be replaced by some or all of the following: LIBS spectrometer, XRD analyzer, Raman spectroscopy equipment, and XRF analyzer.

What is claimed is:
1. An x-ray fluorescence (XRF) analyzer comprising:
   a. an x-ray source having an x-ray emission end, and an x-ray detector having an x-ray receiving end, both carried by a housing;
   b. the x-ray source positioned and oriented to emit x-rays from the x-ray emission end towards a focal point;
   c. the x-ray detector positioned and oriented to face the focal point, and configured to receive, through the x-ray receiving end, fluoresced x-rays emitted from a sample disposed at the focal point;
   d. a rotatable filter cup disposed between the x-ray emission end and the focal point and disposed between the x-ray receiving end and the focal point;
   e. the filter cup being rotatable to separately position:
      i. at least two different x-ray source modification regions (defining source modification regions) between the x-ray emission end and the focal point; and
      ii. at least two different x-ray detector modification regions (defining detector modification regions) between the x-ray receiving end and the focal point.
2. The XRF analyzer of claim 1, wherein:
   a. the filter cup includes an inner cup disposed at least partially inside of an outer cup;
   b. the inner cup and the outer cup each have at least two of the source modification regions and at least one of the detector modification regions;
   c. the inner cup, the outer cup, or both have at least two of the detector modification regions;
   d. the inner cup and the outer cup are rotatable to separately position the source modification regions between the x-ray emission end and the focal point and the detector modification regions between the x-ray receiving end and the focal point;
   e. the inner cup and the outer cup each have a base end opposite of an open end;
   f. the open ends of both the inner cup and the outer cup are disposed between the x-ray emission end and the focal point and between the x-ray receiving end and the focal point; and
   g. a convex portion of the inner cup nests within a concave portion of the outer cup.
3. The XRF analyzer of claim 2, further comprising:
   a. dual, concentric, tubes comprising an inner tube and an outer tube;
   b. the inner tube connected to the inner cup and configured to rotate with the inner cup; and
   c. the outer tube connected to the outer cup and configured to rotate with the outer cup.
4. The XRF analyzer of claim 2, wherein:
   a. the source modification regions on one of the inner cup or the outer cup includes multiple, different solid x-ray filters; and
   b. the source modification regions on the other of the inner cup or the outer cup includes multiple, different collimators sized to collimate x-ray emissions.
5. The XRF analyzer of claim 1, wherein the source modification regions include multiple, different solid x-ray filters.
6. The XRF analyzer of claim 1, wherein the source modification regions include a solid blocking structure having a material and thickness configured to substantially block x-rays from being emitted through the blocking structure.
7. The XRF analyzer of claim 1, wherein the source modification regions include a protective structure compris- ing a solid, protective material configured to protect the x-ray source from damage by solid objects.

8. The XRF analyzer of claim 1, wherein:
   a. the source modification regions include a first collimator having a first diameter and a second collimator having a second diameter; and
   b. the first diameter is substantially different from the second diameter in order to provide a different x-ray collimation at the first collimator relative to the second collimator.

9. The XRF analyzer of claim 1, wherein the detector modification regions include:
   a. a protective structure comprising a solid, protective material configured to protect the x-ray detector from damage by solid objects; and
   b. an aperture configured to allow x-rays to pass therethrough.

10. The XRF analyzer of claim 9, wherein the aperture is a solid x-ray window having a material and thickness to allow x-rays to substantially pass therethrough and to substantially protect the x-ray detector against corrosive chemicals.

11. The XRF analyzer of claim 1, wherein:
    a. the filter cup is hollow with an open end facing the focal point and a base end opposite the open end; and
    b. the filter cup tapers down in diameter from the open end to the base end.

12. The XRF analyzer of claim 11, wherein a cross section of the filter cup at any point from the open end to the base end has a circular shape.

13. The XRF analyzer of claim 11, wherein a cross section of the filter cup at any point between the open end and the base end has a polygon shape.

14. The XRF analyzer of claim 11, further comprising a shaft attached to the base end of the filter cup, the shaft and the filter cup being rotatable to separately position the source modification regions between the x-ray emission end and the focal point and the detector modification regions between the x-ray receiving end and the focal point.

15. The XRF analyzer of claim 1, wherein:
    a. the filter cup is shaped and located to position the source modification regions such that a plane of the source modification regions is substantially parallel to a face of the x-ray emission end; and
    b. the filter cup is shaped and located to position the detector modification regions such that a plane of the detector modification regions is substantially parallel to a face of the x-ray receiving end.

16. The XRF analyzer of claim 1, wherein the XRF analyzer further comprises an electronic processor configured to receive a program, input by a user, and to select and position the source modification regions based on the program.

17. The XRF analyzer of claim 1, wherein the XRF analyzer further comprises an electronic processor configured to analyze x-rays received by the x-ray detector (defining an analysis) and to select and position the source modification regions based on the analysis.

18. A method of using the XRF analyzer of claim 1, the method comprising:
    a. inputting a guess of a material of a sample to be analyzed into the XRF analyzer;
    b. allowing the XRF analyzer to automatically select one of the source modification regions based on the guess;
    c. analyzing the sample (defining an analysis); and
    d. changing the selected source modification region based on the analysis.

19. An x-ray fluorescence (XRF) analyzer comprising:
    a. an x-ray source having an x-ray emission end, and an x-ray detector having an x-ray receiving end, both carried by a housing, wherein:
       i. the x-ray source is positioned and oriented to emit x-rays from the x-ray emission end towards a focal point; and
       ii. the x-ray detector is positioned and oriented to face the focal point, and configured to receive, through the x-ray receiving end, fluoresced x-rays emitted from a sample disposed at the focal point;
    b. a source filter wheel, wherein the source filter wheel:
       i. is rotatable;
       ii. is carried by the housing and is disposed between the x-ray emission end and the focal point;
       iii. has a gear at an outer perimeter; and
       iv. comprises multiple x-ray source modification regions including at least one of:
          1. a first, solid x-ray filter configured to filter x-rays for one x-ray energy band and a second, solid x-ray filter configured to filter x-rays for a different x-ray energy band;
          2. a first, solid x-ray filter having a different thickness than a second, solid x-ray filter;
          3. a first collimator having a first diameter and a second collimator having a second diameter wherein the first diameter is substantially different from the second diameter in order to provide a different x-ray collimation at the first collimator relative to the second collimator;
          4. a solid blocking structure having a material and thickness configured to substantially block x-rays from being emitted through the blocking structure;
          5. a protective structure comprising a solid, protective material configured to protect the x-ray source from damage by solid objects; or
          6. combinations thereof;
    c. a detector filter wheel, wherein the detector filter wheel:
       i. is rotatable;
       ii. is carried by the housing and is disposed between the x-ray receiving end and the focal point;
       iii. has a gear at an outer perimeter; and
       iv. comprises multiple x-ray detector modification regions including:
          1. a protective structure comprising a solid, protective material configured to protect the x-ray detector from damage by solid objects; and
          2. an aperture configured to allow x-rays to pass therethrough;
    d. a gear wheel, wherein the gear wheel:
       i. meshes with the gear on the source filter wheel and the gear on the detector filter wheel; and
       ii. is configured to cause the source filter wheel and the detector filter wheel to rotate together.

20. An x-ray fluorescence (XRF) analyzer comprising:
    a. an x-ray source having an x-ray emission end, and an x-ray detector having an x-ray receiving end, both carried by a housing, wherein:
       i. the x-ray source is positioned and oriented to emit x-rays from the x-ray emission end towards a focal point; and
       ii. the x-ray detector is positioned and oriented to face the focal point, and configured to receive, through the x-ray receiving end, fluoresced x-rays emitted from a sample disposed at the focal point;

b. a filter structure, wherein:
   i. the filter structure is disposed between the x-ray emission end and the focal point;
   ii. the filter structure is disposed between the x-ray receiving end and the focal point;
   iii. the filter structure is rotatable to separately position:
      1. at least two different x-ray source modification regions (defining source modification regions) between the x-ray emission end and the focal point; and
      2. at least two different x-ray detector modification regions (defining detector modification regions) between the x-ray receiving end and the focal point;
   iv. the source modification regions include at least one of:
      1. a first, solid x-ray filter configured to filter x-rays for one x-ray energy band and a second, solid x-ray filter configured to filter x-rays for a different x-ray energy band;
      2. a first, solid x-ray filter having a different thickness than a second, solid x-ray filter;
      3. a solid blocking structure having a material and thickness configured to substantially block x-rays from being emitted through the blocking structure;
      4. a protective structure comprising a solid, protective material configured to protect the x-ray source from damage by solid objects;
      5. a first collimator having a first diameter and a second collimator having a second diameter, wherein the first diameter is substantially different from the second diameter in order to provide a different x-ray collimation at the first collimator relative to the second collimator; or
      6. combinations thereof;
   v. the detector modification regions include:
      1. a protective structure comprising a solid, protective material configured to protect the x-ray detector from damage by solid objects; and
      2. an aperture configured to allow x-rays to pass therethrough.

\* \* \* \* \*